United States Patent [19]
Zoppetti et al.

[11] Patent Number: 5,958,899
[45] Date of Patent: Sep. 28, 1999

[54] POLYSACCHARIDES HAVING A HIGH IDURONIC ACID CONTENT

[75] Inventors: Giorgio Zoppetti; Pasqua Oreste; Giovanni Cipolletti, all of Milan, Italy

[73] Assignee: Inalco S.p.A., Milan, Italy

[21] Appl. No.: 08/628,690

[22] PCT Filed: Oct. 30, 1995

[86] PCT No.: PCT/EP95/04241

§ 371 Date: Apr. 12, 1996

§ 102(e) Date: Apr. 12, 1996

[87] PCT Pub. No.: WO96/14425

PCT Pub. Date: May 17, 1995

[30] Foreign Application Priority Data

Nov. 4, 1994 [IT] Italy ................................. MI94A2240

[51] Int. Cl.$^6$ .......................... A61K 31/715; C08B 37/10
[52] U.S. Cl. ............................... 514/56; 514/54; 536/21; 536/123.1; 536/124
[58] Field of Search ................. 536/123.1, 124, 536/21; 514/54, 56

[56] References Cited

FOREIGN PATENT DOCUMENTS 9217507  10/1992  WIPO .

OTHER PUBLICATIONS

Höök et al. *Biochem. J.* 1974, 137, 33–43, month not available.
"The Merck Index", Ninth Edition, M. Windholz, ed., Merck & Co., Inc., Rahway, NJ, 1976, monograph 4510, pp. 607–608, month not available.
Jensen et al. *Carbohydr. Res.* 1983, 117, 241–253, month not available.
Cöster et al. *Biochem. J.* 1991, 276, 533–539, month not available.
Jacobsson et al. *J. Biol. Chem.* Apr. 25, 1979, 254(8), 2975–2982, month not available.
Kusche et al. *Biochem. J.* 1991, 275(1), 151–158, month not available.
Hook et al., "The J. of Biol. Chem." vol. 249, No. 12, pp. 3908–15 (1994), month not available.
Manzoni et al., "J. of Bioactive and Compatible Polymer", vol. 8, 251–257 (1993), month not available.
Malmstrom et al., "J. of Biol. Chem.", vol. 255, No. 9, 3878–3883 (May 1980), month not available.
Ogamo et al., XIV Int. Carbohydrate Symposium Abstracts p. 302 Aug. 14–19, 1988 Stockholm, Sweden.
Casu et al., Trends Biochem. Sci. "Conformational Flexibility", vol. 13, pp. 221–225 Jun. (1988).
Maccarana et al. Minimal Sequence in Heparin/Heparan Sulfate Required for Binding of Basic Fibroblast Growth Factor, J. Biol. Chem., vol. 268, No. 32, pp. 23898–23905, Nov. (1993).
Coester et al. Biosynthesis of Dermatan Sulfate Proteoglycans' Chemical Abstracts, vol. 115, No. 17, 180062W (1991) month not available.

*Primary Examiner*—Kathleen K. Fonda
*Attorney, Agent, or Firm*—Abelman, Frayne & Schwab

[57] ABSTRACT

Process for the preparation of polysaccharides having a high iduronic acid content comprising:

a) N-deacetylation of the polysaccharide K5 from *E. coli* or of the heparan sulfate or O-desulfation of heparin or heparan sulfate;

b) N-sulfation of the product obtained from the stage a);

c) epimerization in presence of the C5 epimerase enzyme;

d) sulfation of at least some free hydroxy groups, wherein the stage c) is carried out in a reaction medium constituted by a classical buffer solution formed by HEPES, potassium chloride, EDTA and TRITON X-100 to which a suitable additive is added.

8 Claims, 9 Drawing Sheets

POLYSACCHARIDES HAVING A HIGH IDURONIC ACID CONTENT

This application is the U.S. national stage entry under 35 U.S.C. 371 of PCT/EP95/04241, filed Oct. 30, 1995.

PRIOR ART

The glycosaminoglycans which are substances obtained by extraction from animal tissues having various origin, for instance intestinal mucosa, lung, etc. belong particularly to the class of the polysaccharides containing iduronic acid. Heparin, heparan sulfate, condroitin sulfates and hyaluronic acid belong to the family of glycosaminoglycans.

The various glycosaminoglycans have different chemical structures and they are formed by polysaccharide chains constituted by the repetition of an uronic acid and a hexosamine. In particular in heparin and heparan sulfate the uronic acid is constituted by glycuronic or iduronic acid and the hexosamine by glycosamine.

The glycosamine may be preferentially N-acetylated (heparan sulfate) or preferentially N-sulfated (heparin) and 6-0 sulfated. Moreover a sulfate group may be found also in the position 3 of the glycosamine.

The uronic acid may be 2-0 sulfated.

The heparin has great importance in the clinical practice as anticoagulant and antithrombotic.

Besides this therapeutic use an useful utilization for the heparin and the heparan sulfate in several other pathologies, for instance with antilipemic, antiproliferative, antiviral, antitumoral and antiangiogenic function is expected.

The utilization of the heparin and the heparan sulfate in these new therapeutic applications involves the necessity to obtain these products, or similar products, by processes different from the extractive one, in particular by more flexible processes allowing the preparation of different structures.

Moreover the extractive process from animal tissues does not guarantee to obtain a virus free product.

A process for the preparation of anticoagulant glycosaminoglycans by biosynthesis is described in the Patent Application No. WO 92/17507.

In this process the polysaccharide K5 from *E. coli* which is submitted to the following sequence of reactions:

N-deacetylation;

N-sulfation;

epimerization in order to transform at least some residuals of D-glycuronic acid into residuals of L-iduronic acid; and sulfation of at least some free hydroxy groups, is used as a starting compound.

In this process the critical stage is constituted by the epimerization which is limited to a 20% maximum. The epimerization is carried out at room temperature with two days duration in presence of the D-glycuronyl-L-iduronyl-C5-epimerase enzyme in a classical reaction medium to pH 7.4 constituted by HEPES, potassium chloride, EDTA and TRITON X-100. An epimerization limited to one third of the uronic acid had been formerly described (M. Höök et al., The J. of Biol. Chem. 249, 12 3908–3915, Jun. 25, 1974). And this epimerization degree seemed till now insuperable. Moreover it must be considered that in this document the epimerization in cellular environment is described in the murine mastocytoma in conditions in which every factor concerning the biosynthetic process is present.

However an epimerization degree as obtained from the known art does not allow to obtain a product with the requested characteristics for the various therapeutic treatments.

In fact the iduronic acid gives a superior flexibility to the product with respect to the glycuronic acid (Casu B., Petitou M., Provasoli M., and Sinay P. (1988) Conformational flexibility: a new concept for explaining binding and biological properties of iduronic acid containing glycosaminoglycans. Trends Biochem. Sci. 13, 221–225). It follows that the products containing high percentages of iduronic acid are more active with respect to those containing glycuronic acid as it is pointed out by the greater anticoagulant and antithrombotic activity of the heparin towards heparan sulfate and by other activities such as that one on the basic fibroblast growth factor (bFGF) wherein the iduronic acid is recognized to be essential part of the active site (Maccarana M., Casu B., and Lindahl U. (1993). Minimal sequence in Heparin/Heparan Sulfate Required for Binding of Basic Fibroblast Growth Factor. J. Biol. Chem. 268, 23898–23905). Therefore there is the problem to find a process allowing to obtain a product having a high degree of epimerization with yield and times acceptable according to the industrial point of view.

SUMMARY

We have found that polysaccharides having a high iduronic acid content may be obtained starting from the polysaccharide K5 from *E. coli* or from heparin or from the heparan sulfate by a process comprising:

a) N-deacetylation of said polysaccharide K5 or of the heparan sulfate or 0-desulfation of the heparin or of the heparan sulfate;

b) N-sulfation of the product obtained from the stage a);

c) one or more treatments of epimerization in presence of the D-glycuronyl-L-iduronyl-C5-epimerase enzyme;

d) sulfation of at least some free hydroxy groups, characterized in that the stage of epimerization is carried out in a reaction medium constituted by a classical buffer solution at pH 7.4 formed by HEPES, potassium chloride and EDTA to which TRITON X-100 and an additive, or more additives, selected from the group formed by ethylene glycol, glycerol, polyvinylpyrrolidone, polyethylene glycol and phosphatidylcholine are added.

Polysaccharides having iduronic acid content greater than 50% with respect to uronic acids total content are obtained by the process according to the present invention.

DETAILED DESCRIPTION OF THE INVENTION

Figure 1:
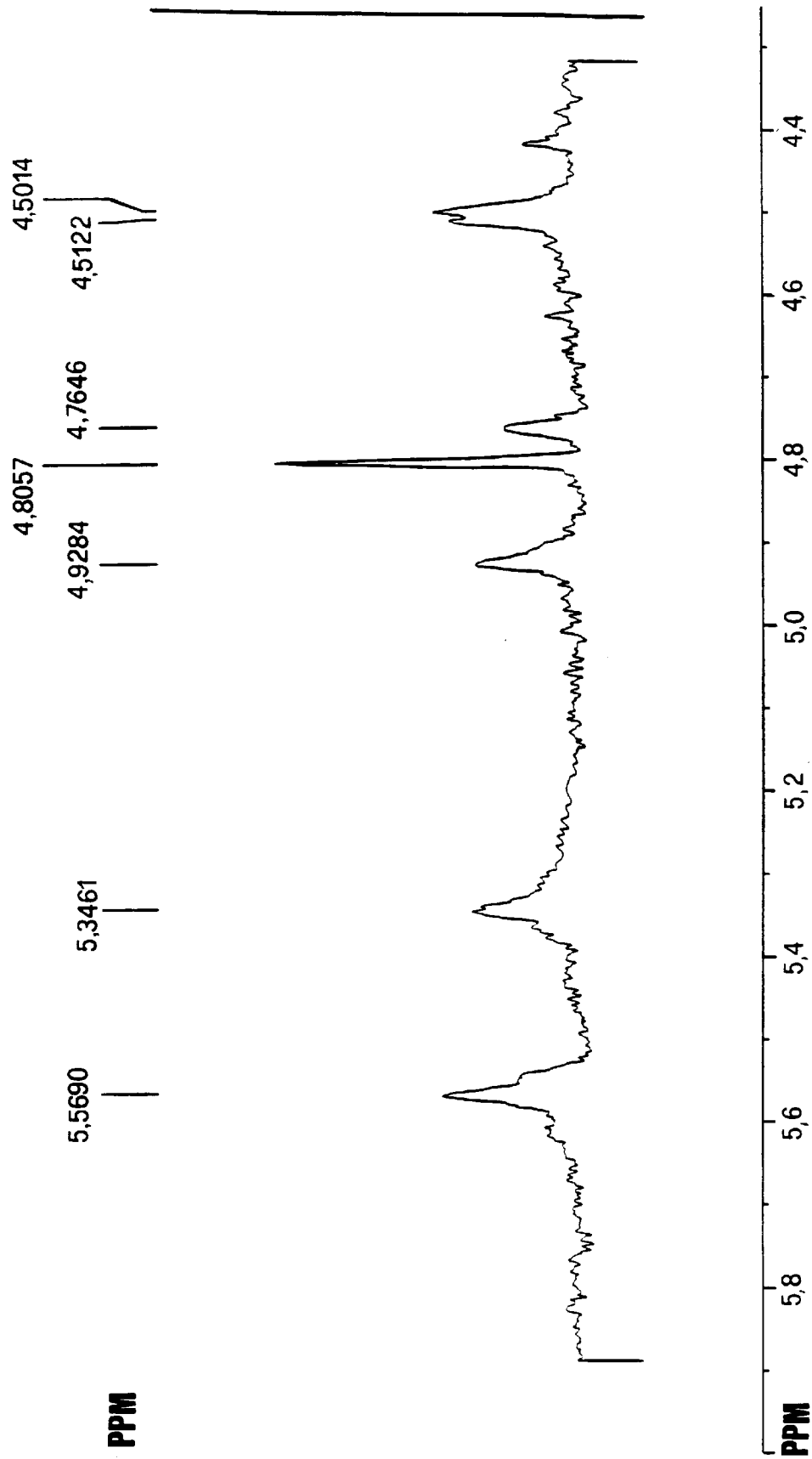
FIG. 1 shows a $^1$H NMR spectrum of the product of Example 1.

The characteristics and the advantages of the process according to the present invention and of the obtained polysaccharides will be mostly pointed out during the following detailed description.

The polysaccharide K5 from *E. coli* described by Manzoni M., Bergomi S., Cavazzoni V. (Journal of Bioactive and Compatible Polymers. Vol. VIII, Jul. 1993, 251–257) is a substance particularly suitable to the use as a starting material for the process according to the present invention.

The heparin and the heparan sulfate may be used too as starting material with some variation of the operative conditions of the first stages of the process.

The starting substances may have a molecular weight ranging from 2,000 to more than 50,000 D.

When the polysaccharide K5 is used its structure is modified first by N-deacetylation which is carried out by treatment with a mixture of hydrazine and hydrazine sulfate or in a basic environment with sodium hydroxide or potassium hydroxide.

Then one proceeds with the N-sulfation by treatment with triethylamine-sulfur trioxide or with trimethylamine-sulfur trioxide. A variously N-sulfated product, for instance from 25% to 100%, may be obtained with these operations.

The reactions of N-deacetylation and N-sulfation are carried out according to the known techniques, for example according to the Patent Application No. WO 92/17507.

When the heparin is used as starting substance first the 0-desulfation and then the N-sulfation are carried out in order to resulfate the amino-positions which lost the sulfate groups during the O-desulfation.

When the heparan sulfate is used as starting substance both the N-deacetylation and the 0-desulfation and the resulting N-resulfation are carried out.

The N-sulfated product obtained from the polysaccharide K5 or from the heparan sulfate as described above, is submitted to the epimerization process in order to convert the glycuronic acid into iduronic acid while the product obtained from heparin is treated with the enzyme in order to obtain the glycuronic acid from the iduronic acid.

The epimerization is carried out in presence of the D-glycuronyl-L-iduronyl-C5-epimerase enzyme (later on simply indicated with C5 epimerase) extracted from cattle liver and purified with the method described by A. Malmstron in J. B. C. 255, 3878–3883 (1980).

The Applicant has surprisingly found that modifying the classical reaction medium with suitable additives a very high degree of epimerization is obtained.

The reaction medium according to the present invention is a pH 7.4 buffer solution constituted by HEPES, potassium chloride, EDTA and TRITON X-100 and added with one or more additives selected from the group formed by ethylene glycol, glycerol, polyvinylpyrrolidone, particularly polyvinylpyrrolidone having molecular weight from 15,000 to 90,000, polyethylene glycol, and phosphatidylcholine in amounts suitable to increase the buffer solution viscosity to values ranging from 1.1 to 3 centistokes.

In particular the reaction medium is prepared starting from the following buffer solution having pH 7.4: HEPES 0.04 M, KC1 0.4 M and EDTA 0.06 M, and to 25 ml of this buffer solution from 100 to 1000 μl of TRITON X-100, from 0.5 ml to 60 ml of additive and distilled water to 100 ml are added.

The polysaccharide to submit to epimerization is added to said reaction medium in an amount from 5 to 1000 mg per 100 ml obtaining the solution A.

The C5 epimerase is separately dissolved in the same above-mentioned reaction medium in amounts from 21 to 2000 μg per 100 ml obtaining the solution B.

The solution B is added to the solution A in such a proportion to obtain a content from 1.5 to 15.000 μg of C5 epimerase per 100 ml of mixture to submit to epimerization. The mixture is homogenized by agitation and warmed at a temperature ranging from 30 to 40° C. in a constant-temperature chamber for a time ranging from 90 minutes to 15 hours.

The reaction is stopped warming the mixture at 100° C. for 5 minutes.

The product is purified through a DEAE-Sephacel column using (NH$_4$)HCO$_3$ 0.05 M as buffer and eluting the product with (HN$_4$)HCO$_3$ 2M buffer.

The gathered fractions are desalted by Sephadex G-15 column, the fraction containing the product is lyophilized and the product is analyzed by 1H-NMR.

The content of D-glycuronic acid and of the L-iduronic acid is computed by 1H-NMR spectrum. The product obtained can be redissolved in solution A and treated again with solution B obtaining, with further treatments of epimerization, an increase of the L-iduronic acid content.

In order to estimate the anticoagulant and antithrombotic activity, the epimerizated product is 0-sulfated using pyridine-sulfur trioxide as sulfating agent for instance with the method described by Ogamo et al. in the abstracts of the XIV International Carbohydrate Symposium (Aug. 14–19, 1988), Stockholm. The products of the Examples 1, 3, 4, 5, 6, 7 and 9, obtained with the process according to the present invention, as later on reported, submitted to 0-sulfation, have shown an excellent anticoagulant and antithrombotic activity while the products of the Examples 2 and 8, obtained according to the known technique, has shown much lower activity.

The obtained results show that the products according to the present invention have characteristics suitable to the clinical use with anticoagulant and antithrombotic function and therefore they may be used for the preparation of the pertaining pharmaceutical compositions mixed with adjuvant and excipient substances.

In order to explain the process according to the present invention the following examples are reported.

EXAMPLE 1

A buffer solution containing 0.04 M HEPES, 0.06 M EDTA, 0.4 M KC1 pH 7.4 was prepared and 27 μl of TRITON X-100, 9 ml of 10% polyvinylpyrrolidone K15 in water, 1.62 ml of ethylene glycol and water to a total volume of 18 ml were added to 4.5 ml of this solution.

The solution showed a viscosity of 1.41 centistokes. In this solution 1 mg of 100% N-deacetylated N-sulfated K5 was dissolved obtaining solution A.

1.6 ml of 10% polyvinylpyrrolidone K15 in water, 288 μl of ethylene glycol and water to a total volume of 3.2 ml were added to 0.8 ml of the same starting buffer solution pH 7.4 containing 8.9 μg of C5 epimerase, obtaining solution B.

Solution A was mixed with 1.6 ml of solution B and the mixture was kept at 37° C. for 4 hours in a warm room. After 4 hours, 1.6 ml of solution B were added and the reaction was kept at 37° C. overnight.

The reaction was stopped by heating at 100° C. for 5 minutes.

The product was purified by a DEAE-Sephacel column (2×1.5 cm) using 0.05 M (HN$_4$)HCO$_3$ as buffer and the product was eluted with 2 M (NH$_4$)HCO$_3$.

The fractions containing the product were desalted on a Sephadex G-15 column (0.3×5 cm) and freeze-dried.

The product was analysed by 1H-NMR and the spectrum is shown in FIG. 1.

The percentage of L-iduronic acid over the total uronic acids was 55.

EXAMPLE 2 (Comparison)

The Example 1 has been repeated with the difference that the polyvinylpyrrolidone and the ethylene glycol have not been added. The used buffer solution had a viscosity about equal to the water, namely about zero.

Figure 2:
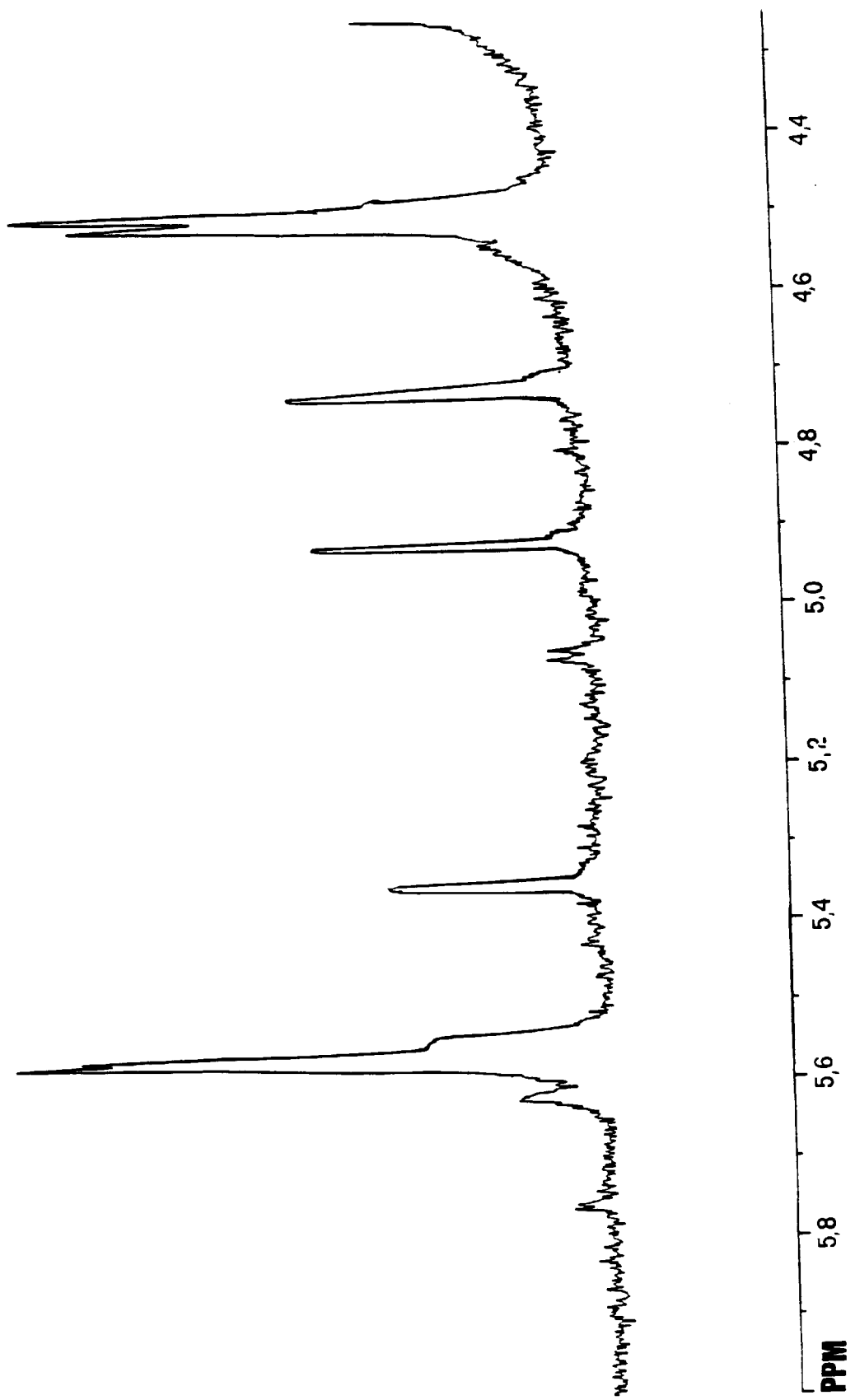
FIG. 2 shows a $^1$H NMR spectrum of the product of Example 2.

The 1H-NMR spectrum relative to the obtained product is reported in the FIG. 2. The L-iduronic acid content with reference to the sum of the iduronic acid and the glycuronic acid turned out to be equal to 18%.

EXAMPLE 3

The Example 1 has been repeated with the difference that the N-deacetylated and 50% N-sulfated polysaccharide K5 has been used as starting substance.

Figure 3:
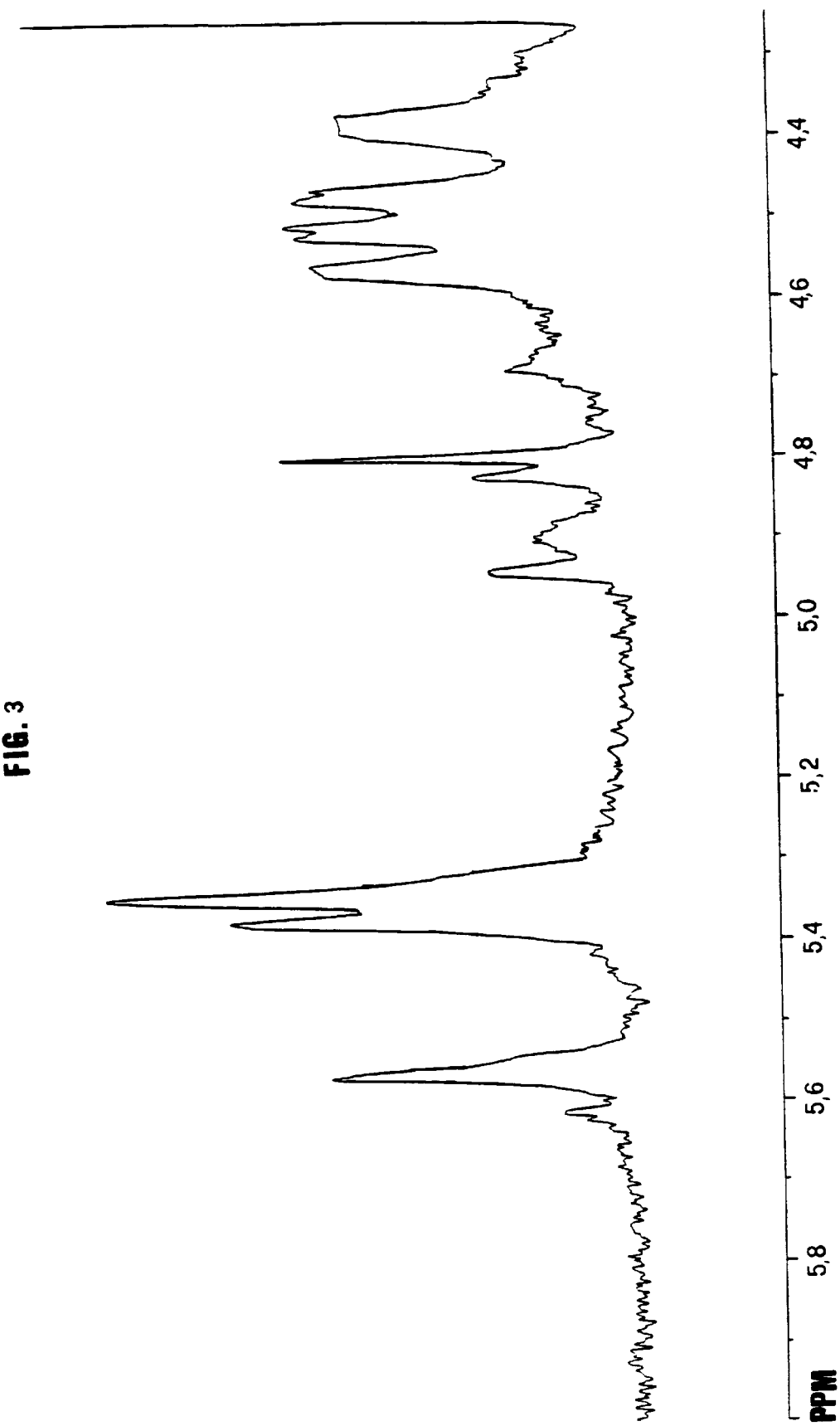
FIG. 3 shows a $^1$H NMR spectrum of the product of Example 3.

The obtained product has been analyzed by 1H-NMR and the relative spectrum is reported in the FIG. 3.

The L-iduronic acid content turned out to be equal to 51% with reference to the total of the uronic acids local to a N-sulfated glucosamine.

EXAMPLE 4

0.06 M EDTA, 0.4 M KCl pH 7.4, 30 $\mu$l of TRITON X-100, 10.6 ml of 10% polyvinylpyrrolidone K15 in water, 0.85 ml of ethylene glycol and 4.42 ml of water were added to 5.3 ml of a buffer solution containing 0.04 M HEPES.

The solution showed a viscosity of 1.2 centistokes.

2 mg of 100% N-deacetylated N-sulfated K5 were dissoled in 9 ml of this solution, obtaining solution A.

1.7 $\mu$g of C5 epimerase were dissolved in 8 ml of the same solution obtaining solution B.

Solutions A and B were mixed and the mixture was kept at 37° C. for 4 hours in a warm room. The reaction was stopped by heating at 100° C. for 5 minutes.

The product was purified as described in Example 1.

After freeze-drying the purified product was dissolved in 1 ml of solution A and mixed with 3.2 ml of solution B containing 8.9 $\mu$g of C5 epimerase.

Figure 4:
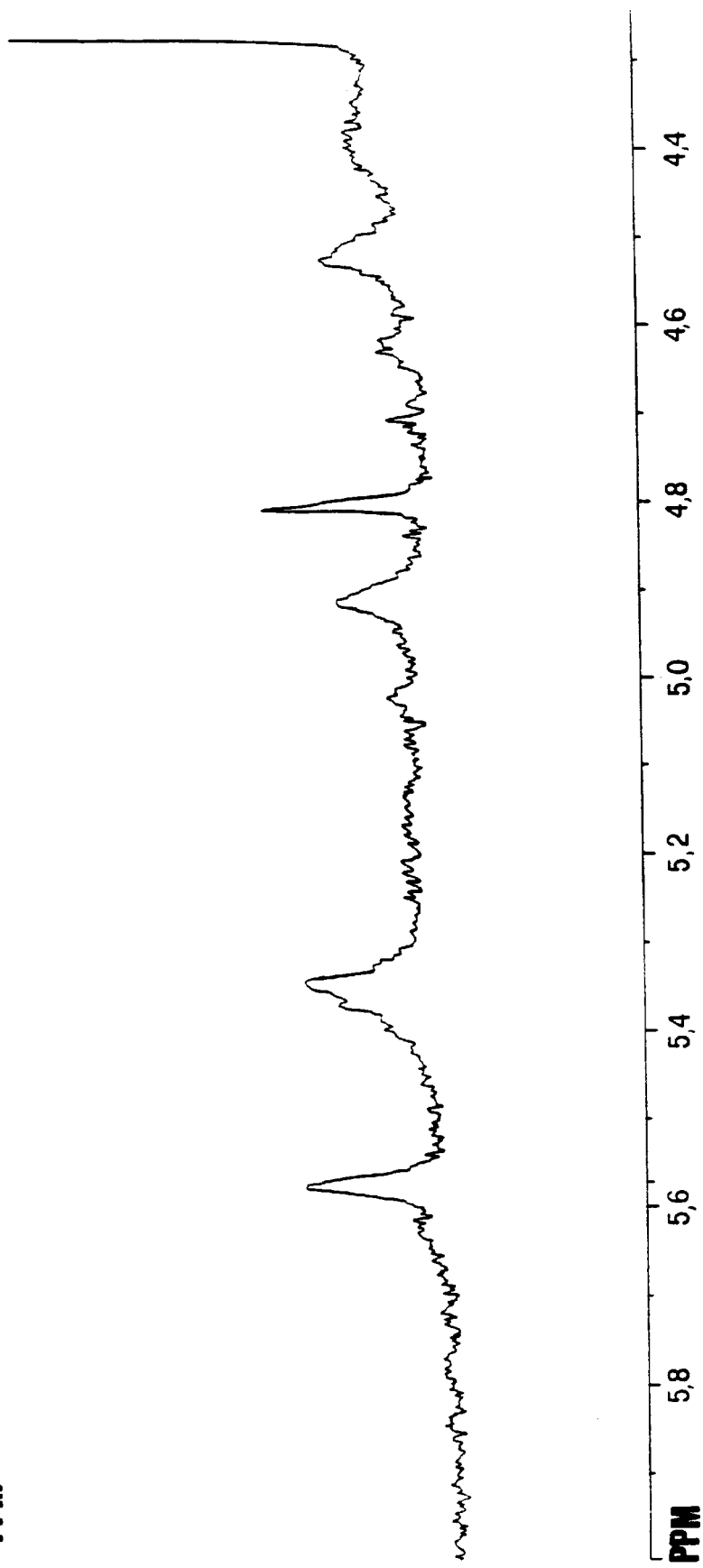
FIG. 4 shows a $^1$H NMR spectrum of the product of Example 4.

The mixture was kept at 370° C. overnight and the enzyme was inactivated by heating at 100° C. for 5 minutes. The product was purified as described in Example 1 and analysed by 1H-NMR as shown in FIG. 4.

The percentage of L-iduronic acid over the total uronic acids was 53.

EXAMPLE 5 buffer solution containing 0.04 M HEPES, 0.06 M EDTA, 0.4 M KCl pH 7.4 was prepared and 22.8 $\mu$l of TRITON X-100, 1 mg of 100% N-deacetylated, N-sulfated K5, 4 ml of a solution of 20% polyvinylpyrrolidone K15 containing 40% ethylene glycol and water to a total volume of 8 ml were added to 2 ml of this solution. 6 ml of a solution containing 0.01 M HEPES, 0.015 M EDTA, 0.01 M KCl, 0.015% TRITON X-100 and 134.4 $\mu$g of C5 epimerase were added to 6 ml of this solution.

The solution obtained showed a viscosity of 1.36 centistokes.

The mixture was kept at 37° C. for 1 hour. The reaction was stopped by boiling at 100° C. for 5 minutes.

The product was purified as described in Example 1.

After freeze-drying the product was dissolved in buffer solution containing 6.25 ml of 0.04 M HEPES, O.o6 M EDTA, 0.4 M KCl pH 7.4, 2.5 g of polyvinylpyrrolidone K15, 2.5 ml of ethylene glycol, 71.2 $\mu$l of TRITON X-100 and water to a total volume of 25 ml.

1.9 $\mu$g of C5 epimerase dissolved in 12 ml of 0.01 M HEPES, 0.015 M EDTA, 0.1 M KCl pH 7.4 containing 0.015% of TRITON X-100 were added to 12 ml of the obtained mixture.

The mixture showed a viscosity of 1.4 centistokes.

Figure 5:
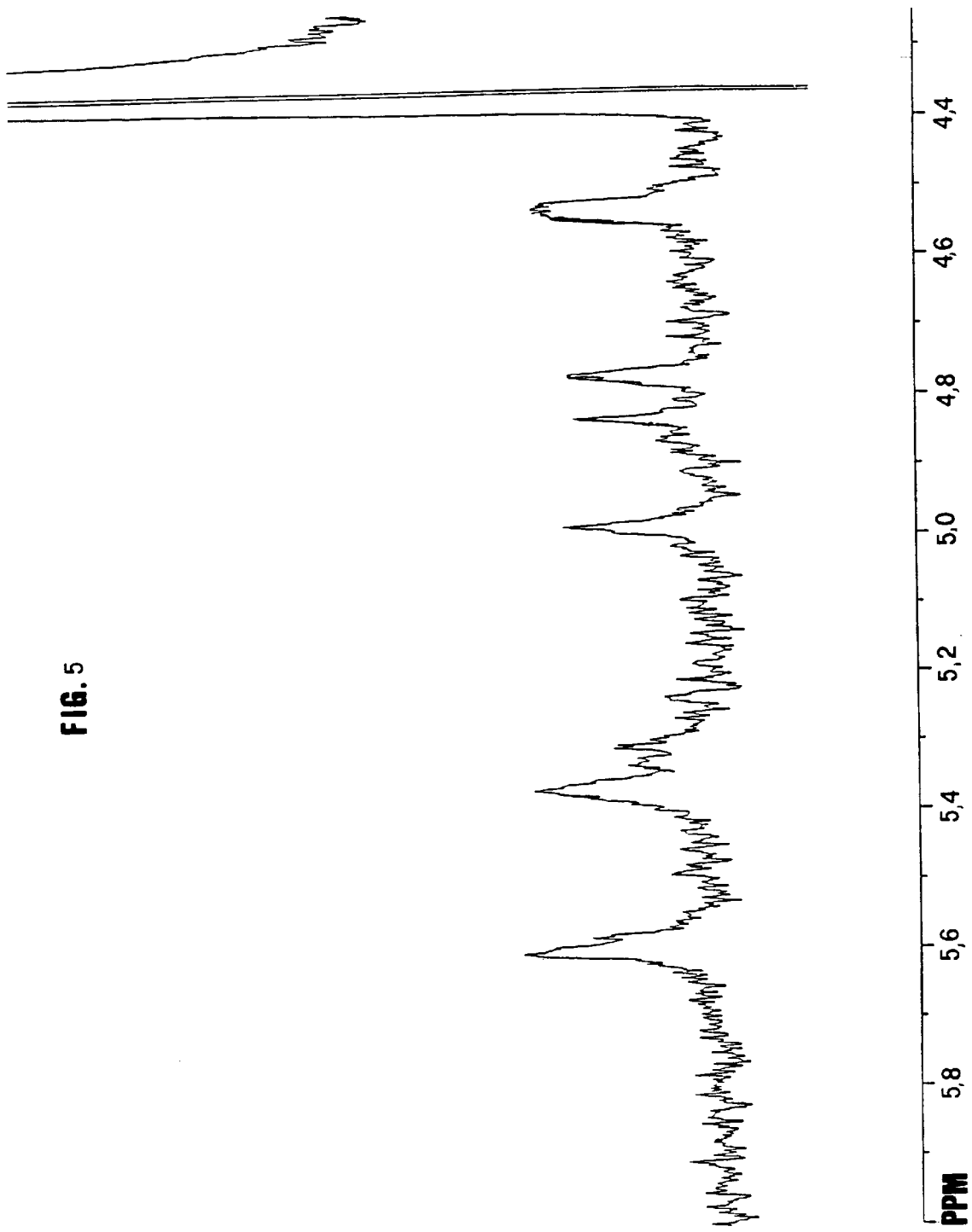
FIG. 5 shows a $^1$H NMR spectrum of the product of Example 5.

The reaction was kept at 37° C. overnight, At the end of the reaction the enzyme was inactivated by heating the solution at 100° C. for 5 minutes. The product was purified as described in example 1 and the 1H-NMR spectrum was performed (FIG. 5).

The percentage of L-iduronic acid over the total uronic acids was 52.

EXAMPLE 6

The Example 5 was repeated except that in the first step the reaction was kept at 37° C. for 4 hours.

After purification in the same conditions of Example 1 and after freeze-drying the product was dissolved in 1 ml of water and added to a buffer solution containing 50 ml of 0.04 M HEPES, 0.06 M EDTA, 0.4 M KCl pH 7.4, 283.5 $\mu$l of TRITON X-100, 100 ml of 10% polyvinylpyrrolidone K15, 20 ml of ethylene glycol, 2 ml of 90% glycerol, 1.9 $\mu$g of C5 epimerase and water to a total volume of 200 ml. The mixture showed a viscosity of 1.41 centistokes.

The reaction was kept at 37° C. for 4 hours and the enzyme was inactivated at 100° C. for 5 minutes.

Figure 6:
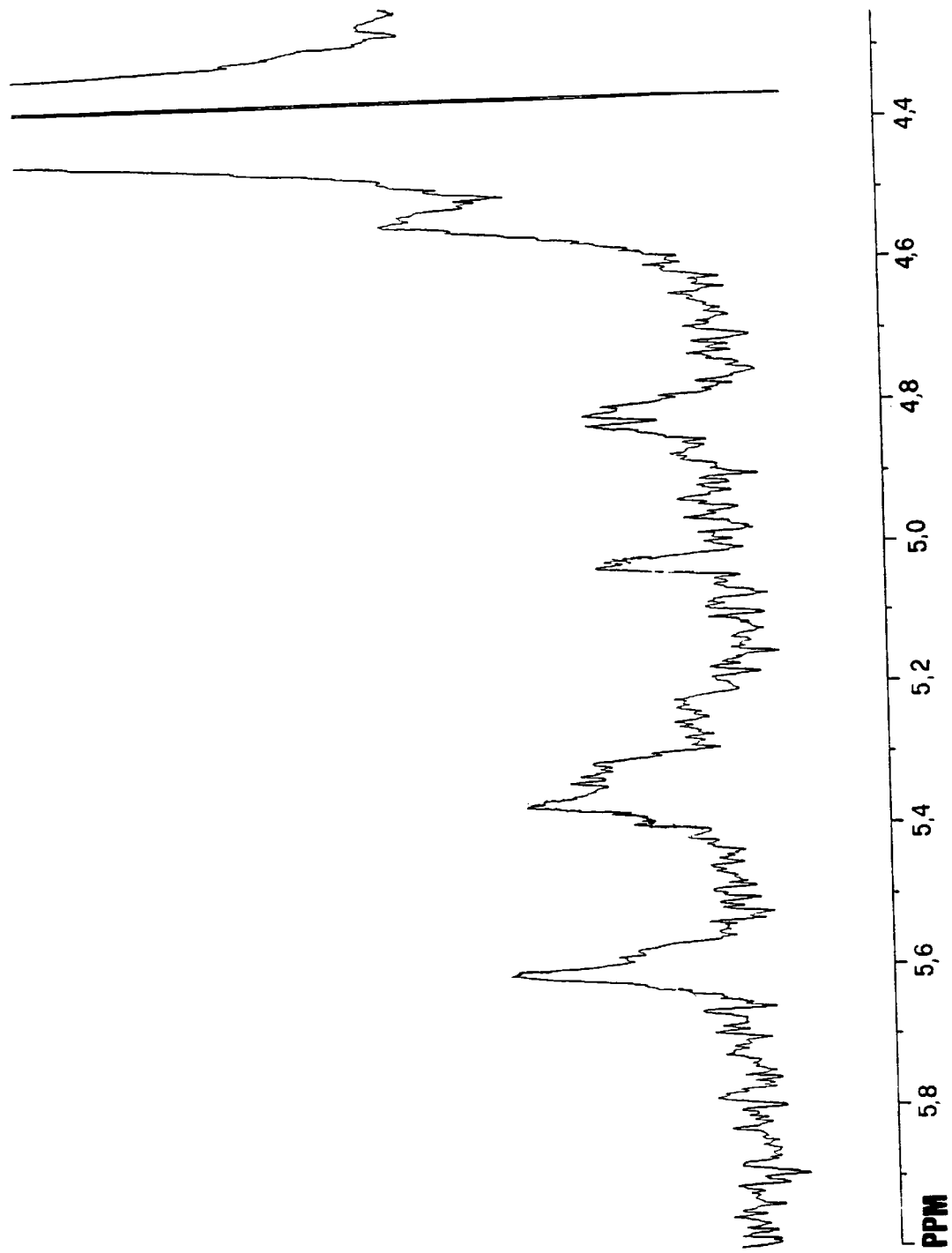
FIG. 6 shows a $^1$H NMR spectrum of the product of Example 6.

The product was purified as described in Example 1 and the 1H-NMR spectrum was performed (FIG. 6).

The percentage of L-iduronic acid over the total uronic acids was 55.

EXAMPLE 7

1.5 mg of 100% N-deacetylated, AT-sulfated K5 were dissolved in a buffer solution containing 7 ml of 0.04 M HEPES, 0.06 M EDTA, 0.4 M KCl pH 7.4, 210 $\mu$l of TRITON X-100, 1.4 g of polyvinylpyrrolidone K15, 2.8 ml of ethylene glycol, 1.5 mg of C5 epimerase and water to a total volume of 28 ml.

The solution showed a viscosity of 1.36 centistockes.

The reaction was kept at 37° C. for 4 hours and the enzyme was inactivated at 100° C. for 5 minutes.

The product was purified as described in Example 1 and freeze-dried. The product was then dissolved in 24 ml of the same solution containing 1.3 mg of C5 epimerase and the reaction was kept at 37° C. for 4 hours and the enzyme was inactivated at 100° C. for 5 minutes. The product was purified as described in Example 1 and freeze-dried. The product was then dissolved in 8.4 ml of the same solution containing 1 mg of C5 epimerase and the reaction was kept at 37° C. for 4 hours.

Figure 7:
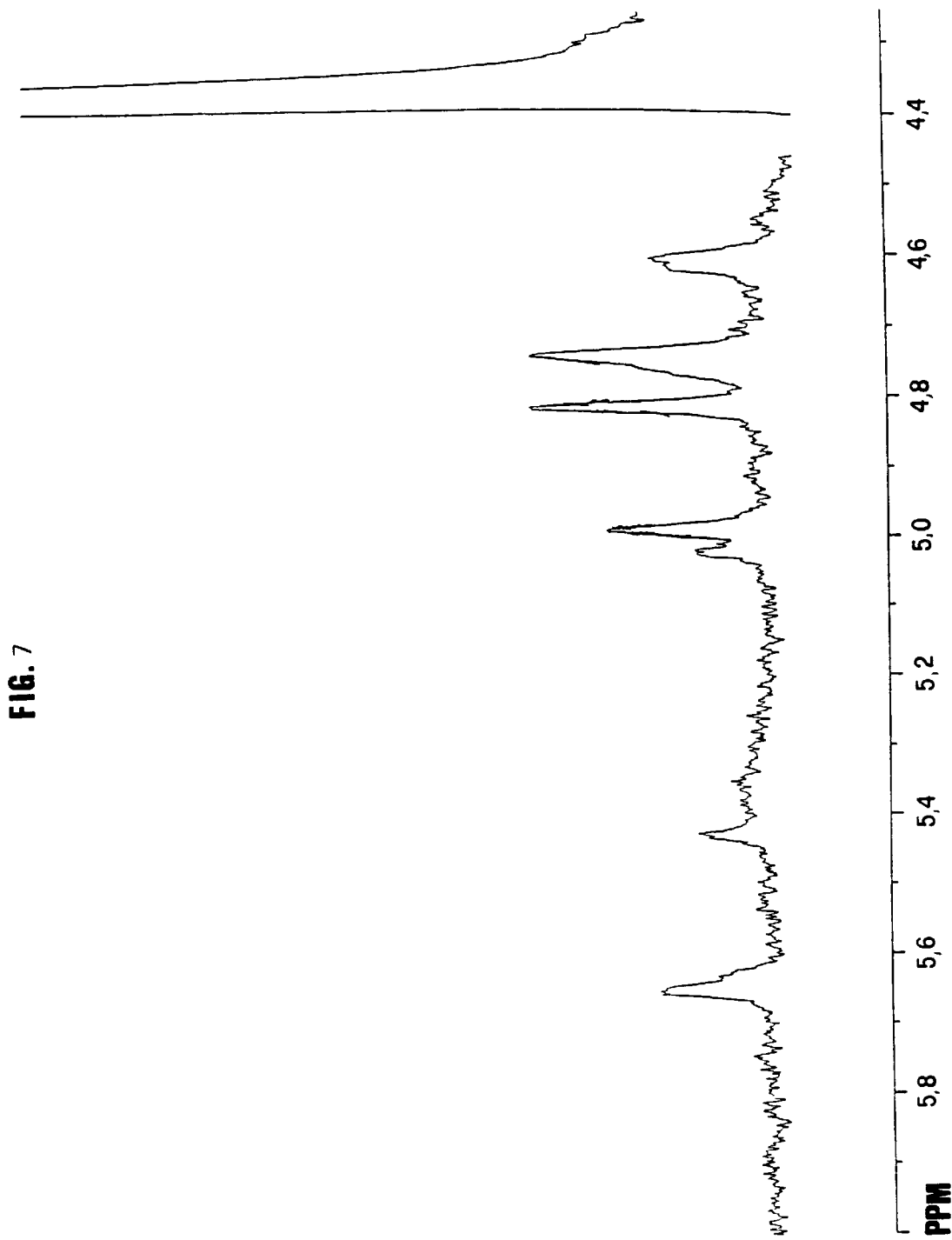
FIG. 7 shows a $^1$H NMR spectrum of the product of Example 7.

The product was purified as described in Example 1 and the 1H-NMR spectrum was performed (FIG. 7).

The percentage of L-iduronic acid over the total uronic acids was 80.

EXAMPLE 8 (comparison)

1 mg of 100% N-deacetylated, N-sulfated K5 was dissolved in a buffer solution containing 3 ml of 0.04 M HEPES, 0.06 M EDTA, o.4 M KCl pH 7.4, 18 µl of TRITON X-100, 1.2 ml of acetone, 1.9 µg of C5 epimerase and water to a total volume of 12 ml.

The solution showed a viscosity of 0.09 centistokes.

The reaction was kept at 37° C. for 4 hours.

Figure 8:
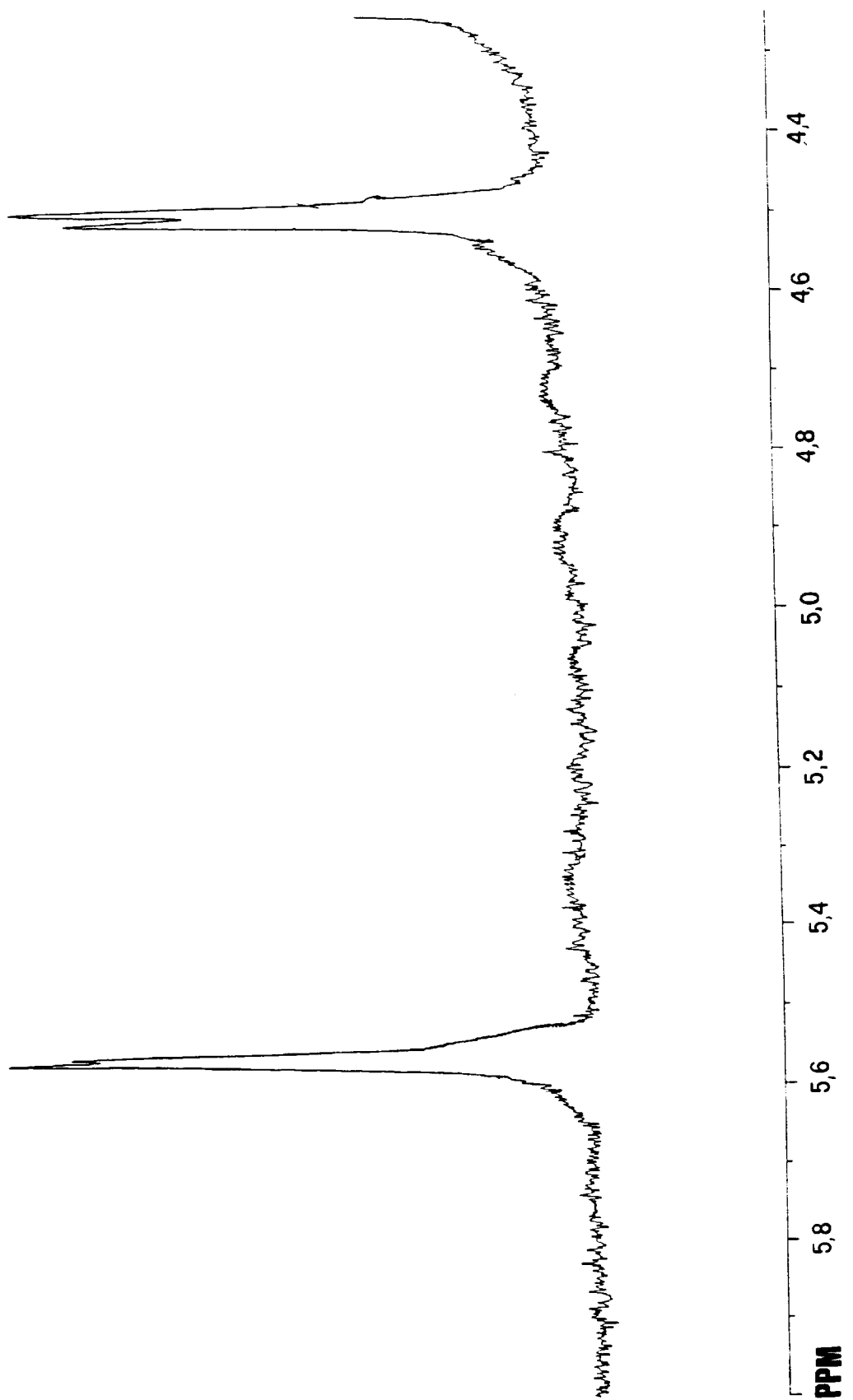
FIG. 8 shows a $^1$H NMR spectrum of the product of Example 8.

The product was purified as described in Example 1 and the 1H-NMR spectrum was performed (FIG. 8).

The percentage of L-iduronic acid over the total uronic acids was 0.

EXAMPLE 9

1 mg of 100% N-deacetylated, N-sulfated K5 was dissolved in a buffer solution containing 2 ml of 0.04 M HEPES, o.06 M EDTA, 0.4 M KCl pH 7.4, 12 µl of TRITON X-100, 1.336 ml of 2.4% polyvinylpyrrolidone K90, 304 µg of C5 epimerase and water to a total volume of 8 ml.

The solution showed a viscosity of 1.29 centistokes.

The reaction was kept at 37° C. for 4 hours, the enzyme was inactivated at 100° C. for 5 minutes and the solution filtered in a 0.22 µm device. 8 ml of the same mixture containing 304 µg of C5 epimerase were added to the filtered solution and the reaction was kept at 37° C. for 4 hours, the enzyme Was inactivated at 100° C. for 5 minutes and the solution filtered in a 0.22 µm device.

8 ml of the same mixture containing 304 µg of C5 epimerase were added to this solution and the reaction was kept at 37° C. for 4 hours, the enzyme was inactivated at 100° C. for 5 minutes and the solution filtered in a 0.22 µm device.

Figure 9:
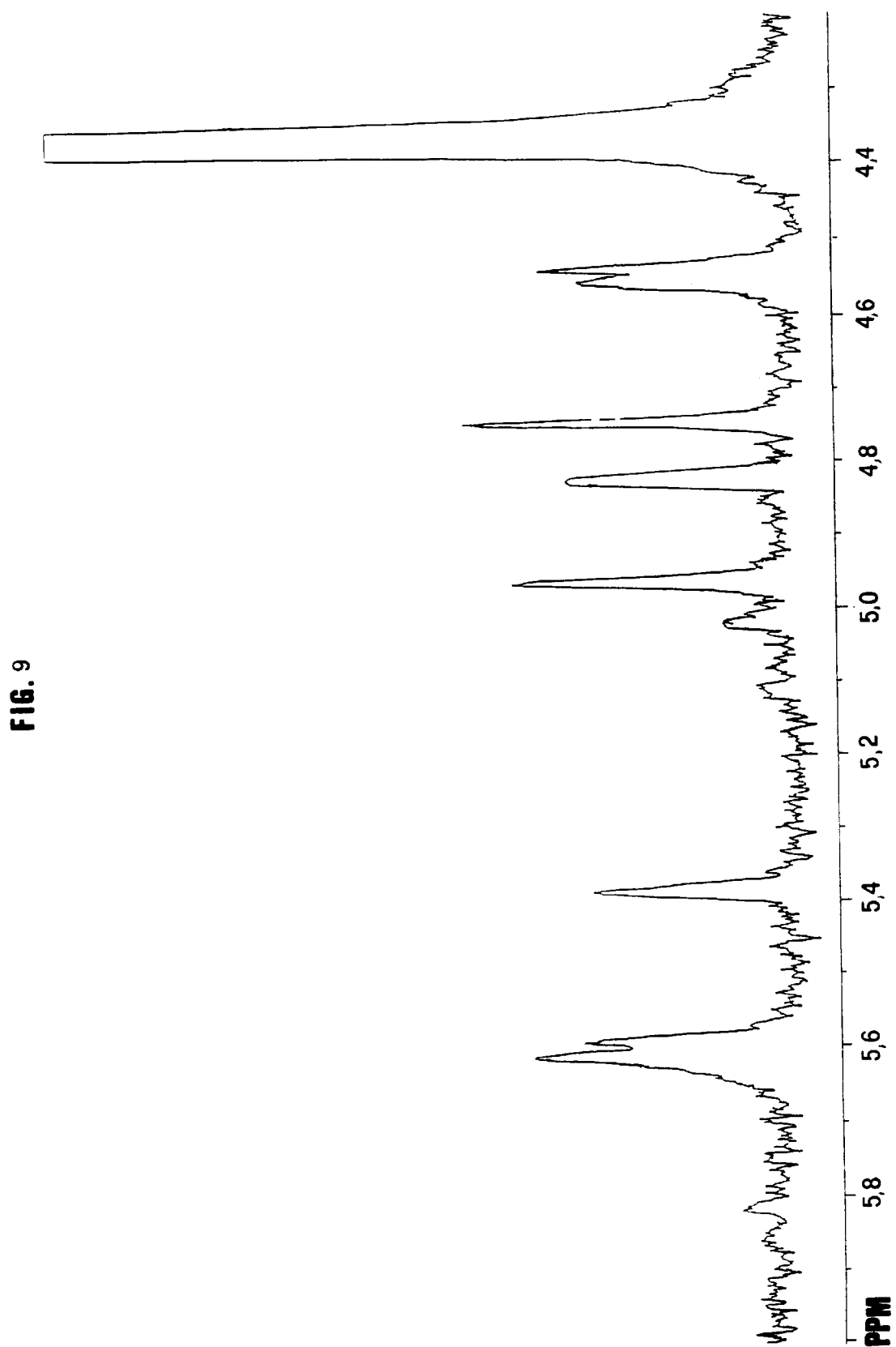
FIG. 9 shows a $^1$H NMR spectrum of the product of Example 9.

The product was purified as described in Example 1 and the 1H-NMR spectrum was performed (FIG. 9).

The percentage of L-iduronic acid over the total uronic acids was 59.

We claim:

1. Process for the preparation of polysaccharides having a L-iduronic acid content greater than 50% with reference to the uronic acids total content starting from polysaccharide k5 of *E. coli* or from heparin or from heparan sulfate, comprising:

a) N-deacetylation of said polysaccharide k5 or of said heparan sulfate or O-desulfation of said heparin or heparan sulfate;

b) N-sulfation of the product obtained from the stage a);

c) one or more treatments of epimerization in presence of C5 epimerase enzyme;

d) sulfation of at least some free hydroxy groups, wherein the epimerization treatment or treatments are carried out in a reaction medium consisting of a classicial buffer solution at pH 7.4 comprising HEPES, potassium chloride and EDTA to which TRITON X-100 and one or more additives in an amount suitable to increase the viscosity of said buffer solution to values ranging from 1.1 to 3 centistokes are added.

2. Process as claimed in claim 1, wherein said additive or additives are selected from the group consisting of ethylene glycol, glycerol, polyvinylpyrrolidone, polyethylene glycol and phosphatidylcholine.

3. Process as claimed in claim 1, wherein said additive is polyvinylpyrrolidone having molecular weight from 15,000 to 90,000.

4. Process as claimed in claim 1 wherein said additive, or additives, are added to said buffer solution in an amount from 2 to 240 ml with reference to 100 ml of said buffer solution.

5. Process as claimed in claim 1 wherein said starting compounds are dissolved in said reaction medium in an amount from 5 to 1000 mg per 100 ml.

6. Process as claimed in claim 1, wherein said C5 epimerase is dissolved in said reaction medium in an amount from 21 to 2000 µg per 100 ml.

7. Process as claimed in claim 1, wherein said epimerization treatment or treatments are carried out in a constant-temperature chamber at a temperature ranging from 30 to 40° C.

8. Process as claimed in claim 1, wherein said starting products are N-sulfated from 25% to 100%.

* * * * *